US009383294B2

(12) United States Patent
Kenney et al.

(10) Patent No.: US 9,383,294 B2
(45) Date of Patent: Jul. 5, 2016

(54) HYDROPHILIC FLUID TRANSPORT DEVICE

(71) Applicant: 3M INNOVATIVE PROPERTIES COMPANY, St. Paul, MN (US)

(72) Inventors: Raymond J. Kenney, Woodbury, MN (US); Theresa J. Gerten, Inver Grove Heights, MN (US); Daniel P. Decabooter, Woodbury, MN (US); Naiyong Jing, Woodbury, MN (US); Garry W. Lachmansingh, Plymouth, MN (US)

(*) Notice: Subject to any disclaimer, the term of this patent is extended or adjusted under 35 U.S.C. 154(b) by 98 days.

(21) Appl. No.: 14/355,465

(22) PCT Filed: Oct. 30, 2012

(86) PCT No.: PCT/US2012/062583
§ 371 (c)(1),
(2) Date: Apr. 30, 2014

(87) PCT Pub. No.: WO2013/066874
PCT Pub. Date: May 10, 2013

(65) Prior Publication Data
US 2014/0299193 A1    Oct. 9, 2014

Related U.S. Application Data

(60) Provisional application No. 61/554,553, filed on Nov. 2, 2011.

(51) Int. Cl.
*G01N 21/75* (2006.01)
*G01N 1/28* (2006.01)
(Continued)

(52) U.S. Cl.
CPC ............ *G01N 1/28* (2013.01); *B01L 3/502707* (2013.01); *C08J 7/047* (2013.01);
(Continued)

(58) Field of Classification Search
CPC ................... B01L 2200/12; B01L 2300/0861; B01L 3/508; B01L 2400/0406; B01L 3/502; B01L 2300/0816; B01L 2300/0819; B01L 2300/0851; B01L 2300/16; B01L 2300/161; B01L 2400/0487; B01L 3/502707; B01L 2300/0645; B01L 2300/0864; G01N 1/02; G01N 1/10; G01N 2035/1055; C08J 2323/06; C08J 2483/04; C08J 7/047; C09D 7/1216; C09D 7/1266; Y10T 137/0318; Y10T 137/8593
See application file for complete search history.

(56) References Cited

U.S. PATENT DOCUMENTS 2,366,516 A    1/1945  Walter
2,432,484 A   12/1947  Moulton
(Continued)

FOREIGN PATENT DOCUMENTS

WO    WO 2011-124906    10/2011
WO    WO 2014-046955     3/2014

OTHER PUBLICATIONS

International Search Report for PCT International Application No. PCT/US2012/062583, mailed on Feb. 14, 2013, 4 pages.
(Continued)

*Primary Examiner* — Dennis M White

(57) ABSTRACT

Hydrophilic articles and methods of using such articles are described. The hydrophilic articles include a hydrophilic layer comprising sintered, acidified silica nanoparticles attached to a substrate. A spacer layer attached to a first portion of the hydrophilic layer defines at least one fluid transport channel bounded on one side by a second portion of the hydrophilic layer. The nanoparticles may include one or both of spherical and elongated nanoparticles.

19 Claims, 3 Drawing Sheets

(51) Int. Cl.
*B01L 3/00* (2006.01)
*C09D 7/12* (2006.01)
*C08J 7/04* (2006.01)

(52) U.S. Cl.
CPC .......... *C09D 7/1216* (2013.01); *C09D 7/1266* (2013.01); *B01L 2300/0645* (2013.01); *B01L 2300/0816* (2013.01); *B01L 2300/0864* (2013.01); *B01L 2300/161* (2013.01); *B01L 2400/0406* (2013.01); *C08J 2323/06* (2013.01); *C08J 2483/04* (2013.01); *Y10T 137/0318* (2015.04); *Y10T 137/8593* (2015.04)

(56) References Cited

U.S. PATENT DOCUMENTS

| | | |
|---|---|---|
| 2,536,764 A | 1/1951 | Moulton |
| 2,601,123 A | 6/1952 | Moulton |
| 4,816,333 A | 3/1989 | Lange |
| 5,585,186 A | 12/1996 | Scholz |
| 5,723,175 A | 3/1998 | Scholz |
| 5,753,373 A | 5/1998 | Scholz |
| 6,040,053 A | 3/2000 | Scholz |
| 6,375,871 B1 | 4/2002 | Bentsen |
| 7,223,364 B1 | 5/2007 | Johnston |
| 7,378,451 B2 | 5/2008 | Levitt |
| 7,476,533 B2 | 1/2009 | Meathrel |
| 2010/0035039 A1 | 2/2010 | Jing |
| 2010/0092765 A1 | 4/2010 | Hager |
| 2011/0033694 A1 | 2/2011 | Jing |

OTHER PUBLICATIONS

Shang, "Optically transparent superhydrophobic silica-based films", Thin Solid Films, 2005, vol. 472, pp. 37-43.

HYDROPHILIC FLUID TRANSPORT DEVICE

CROSS REFERENCE TO RELATED APPLICATIONS

This application is a national stage filing under 35 U.S.C. 371 of PCT/US2012/062583, filed Oct. 30, 2012, which claims priority to U.S. Provisional Application No. 61/554,553, filed Nov. 2, 2011, the disclosures of which are incorporated by reference in their entirety herein.

FIELD

The present disclosure relates to hydrophilic articles, including those capable of providing fluid transport. Articles incorporating hydrophilic layers including sintered, acidified nanoparticles are described. The present disclosure also relates to methods of making and using hydrophilic fluid transport articles.

SUMMARY

Briefly, in one aspect, the present disclosure provides a hydrophilic article comprising a substrate, a first surface of a hydrophilic layer comprising sintered, acidified silica nanoparticles attached to the substrate, and a spacer layer attached to a first portion of a second surface of the hydrophilic layer opposite the first surface. The spacer layer defines at least one fluid transport channel bounded on one side by a second portion of the hydrophilic layer.

In some embodiments, the hydrophilic article further comprises a cover layer attached to the spacer layer and covering at least a portion of the fluid transport channel. In some embodiments, the fluid transport channel comprises a landing zone comprising an exposed portion of the hydrophilic layer. In some embodiments, the fluid transport channel comprises a detection zone. In some embodiments, the hydrophilic article comprises a cover layer in contact with at least a portion of a surface of the spacer layer opposite the hydrophilic layer, e.g., a cover layer comprising a second hydrophilic layer comprising sintered, acidified silica nanoparticles attached to a second substrate.

In some embodiments, the nanoparticles comprise elongated silica nanoparticles having an average length to diameter ratio of at least 2, e.g., 3 to 15. In some embodiments, the nanoparticles comprise substantially spherical silica nanoparticles having a ratio of maximum diameter to minimum diameter of less than 2, e.g., less than 1.2. In some embodiments, the nanoparticles comprise 50 to 95 weight percent substantially spherical silica nanoparticles having a ratio of maximum diameter to minimum diameter of less than 2, and 5 to 50 parts by weight elongated silica nanoparticles having an average length to diameter ratio of at least 2, based on the total weight of the nanoparticles.

In some embodiments, the hydrophilic layer comprises at least 95 weight percent of the nanoparticles. In some embodiments, the hydrophilic layer comprises no greater than 5 weight percent resin. In some embodiments, the hydrophilic layer consists essentially of the nanoparticles.

In another aspect, the present disclosure provides a method of transporting a fluid with a hydrophilic article of the present disclosure. Such methods comprise applying the fluid to a first region of the second portion of the second surface of the hydrophilic layer and wicking the fluid within the fluid transport channel from the first region to a second region of the second portion of the second surface of the hydrophilic layer. In some embodiments, the fluid is a biological fluid.

The above summary of the present disclosure is not intended to describe each embodiment of the present invention. The details of one or more embodiments of the invention are also set forth in the description below. Other features, objects, and advantages of the invention will be apparent from the description and from the claims.

DETAILED DESCRIPTION

Certain devices such as fluidic diagnostic test devices conduct fluid from a first position to a second position, e.g. from a source to a detection region of the device. Generally, fluidic diagnostic test devices include a substrate made from one or more materials selected to provide certain desirable qualities to the device. For example, substrates often include polymeric films, which provide desired mechanical properties. However, most polymeric films are hydrophobic and do not promote transport of fluids, particularly aqueous solutions such as bodily fluids, to an extent sufficient to provide the device with a desired level of performance. Therefore, most polymeric films require some form of surface treatment or coating to render them sufficiently hydrophilic to provide fluid transport.

Products suitable for fluid transport applications can be produced using surfactant-containing systems. For example, as described in U.S. Pat. No. 7,378,451 ("Surfactant Composition having Stable Hydrophilic Character," Levitt and Scholz, issued May 27, 2008), a surfactant coating on at least a portion of the substrate can provide physical or chemical properties that promote fluid transport and, therefore, improve performance of the device. However, the use of surfactants can result in undesirable attributes. For example, some surfactant chemistries impart haze, which can be undesirable, particularly in applications designed for diagnostic devices that rely on optical interrogation methods. Also, surfactants tend to be fugitive and the hydrophilicity they impart can diminish with time; thus, limiting the product's shelf life. The fugitive nature of the surfactants can also lead to contamination of fluids contacting them during use and interfere with subsequent analyses of such fluids. For example, surfactant contamination can interfere with the chemical or electrochemical assay detection in devices using hydrophilic films as capillary flow devices, e.g., diabetes glucose monitors and their associated test strips. In addition, it can be difficult to bond adhesives, including pressure sensitive adhesives, to many surfactant-containing coatings.

Figure 1:
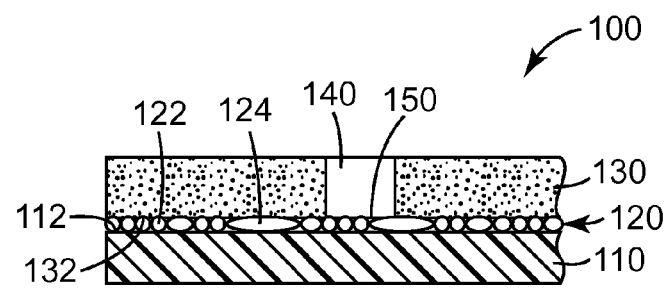
FIG. 1 illustrates an edge view of an exemplary hydrophilic article according to some embodiments of the present disclosure.
Figure 2:
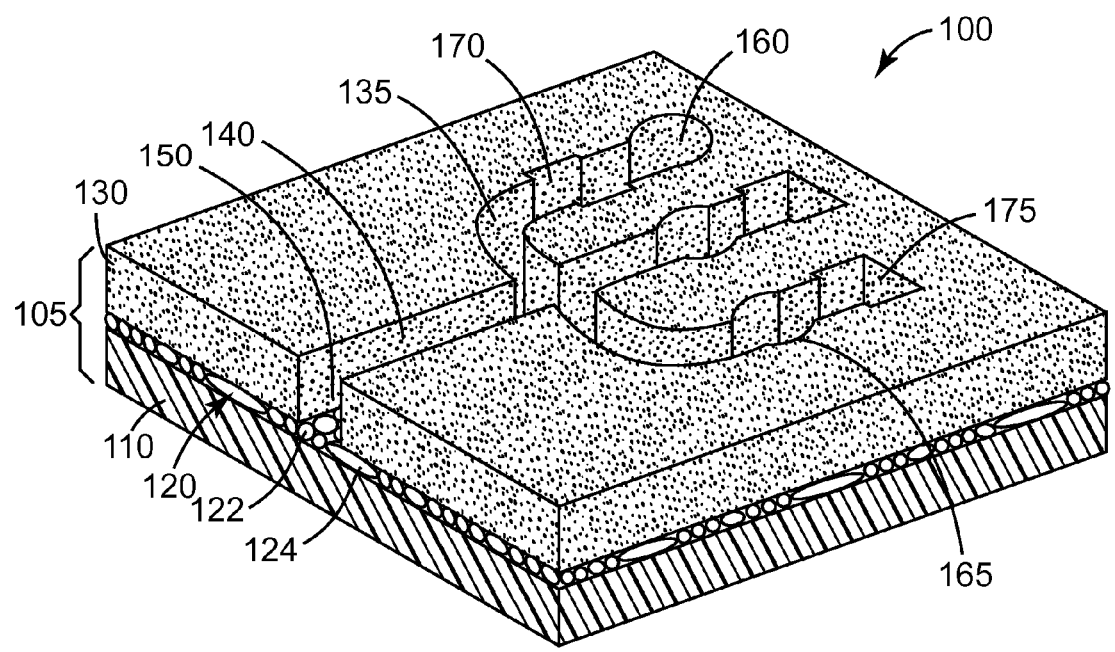
FIG. 2 illustrates a perspective view of the exemplary hydrophilic article of FIG. 1 according to some embodiments of the present disclosure.
Figure 3:
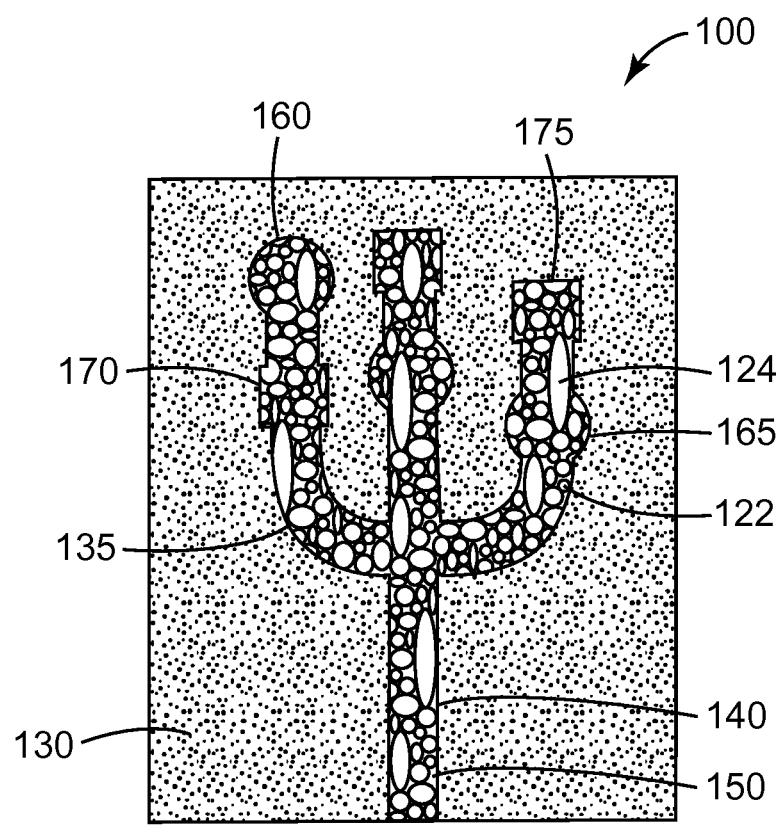
FIG. 3 illustrates a top view of the exemplary hydrophilic article of FIG. 1 according to some embodiments of the present disclosure.

The present inventors have discovered that a hydrophilic layer can be prepared from sintered, acidified silica nanoparticles. In some embodiments, the hydrophilic layer is substantially surfactant-free. As used herein, a "surfactant" is an amphiphilic organic compound. Ideally, a surfactant-free material would not contain any amphiphilic organic compounds. However, as a practical matter this may be difficult or impossible to achieve. For example, trace amounts of such materials may be present in purchased or manufactured raw materials, or may arise as contaminants in a particular manufacturing process. As used herein, a material is "substantially surfactant-free" if it contains less than 0.002 wt. % amphiphilic organic compounds based on the total weight of the material. In some embodiments, substantially surfactant-free materials contain no greater than 0.001 wt. % or even no greater than 0.0005 wt. % amphiphilic organic compounds based on the total weight of the material One exemplary hydrophilic article 100 according to some embodiments of the present disclosure is shown in FIGS. 1 through 3. Hydrophilic article 100 comprises substrate 110, hydrophilic layer 120, and spacer layer 130. Generally, hydrophilic layer 120 is located between substrate 110 and spacer layer 130.

In some embodiments, hydrophilic layer 120 is directly attached to first surface 112 of substrate 110. In some embodiments, hydrophilic layer 120 may be indirectly attached to substrate 110, i.e., one or more additional layers, e.g., adhesive layers or primer layers, may be located between the hydrophilic layer and the substrate.

Similarly, in some embodiments, hydrophilic layer 120 may be directly attached to first surface 132 of spacer layer 130. In some embodiments, hydrophilic layer 120 may be indirectly attached to spacer layer 130, i.e., one or more additional layers, e.g., adhesive layers or primer layers, may be located between the hydrophilic layer and the spacer layer.

Generally, spacer layer 130 only covers a portion of the hydrophilic layer. The gaps in coverage create fluid transport channel 140. Fluid transport channel 140 is bounded on one side by the surface of hydrophilic layer 120 left exposed by the gaps in coverage by the spacer layer. The exposed edges of spacer layer 130 create the walls 135 defining the boundaries of fluid transport channel 140. Generally, walls 135 constrain fluid with the fluid transport channel. Generally, hydrophilic layer 120 facilitates the transport along the channel between walls 135, and substantially prevents the flow of fluid under spacer layer 130.

Generally, the fluid transport channel can have any dimensions and may take on any configuration suitable for the intended application. FIGS. 2 and 3 illustrate one exemplary fluid transport channel containing certain generic features that may be beneficial in certain applications. Particular features illustrated in FIGS. 2 and 3 may be used alone or in combination with other features, including unillustrated features.

Figure 4:
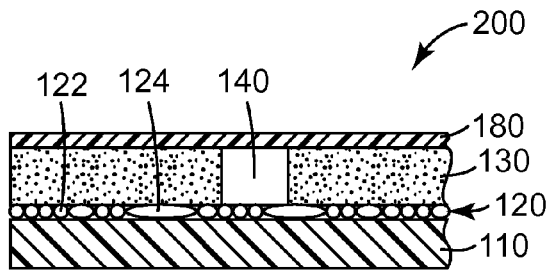
FIG. 4 illustrates an edge view of another exemplary hydrophilic article according to some embodiments of the present disclosure.

For example, in some embodiments, fluid transport channel 140 includes landing zone 150. As used herein, "landing zone" means a location allowing fluid to be introduced into the fluid transport channel. In some embodiments, the landing zone may be located at an edge of the hydrophilic article. For example, as shown in FIGS. 3 and 4, landing zone 150 is proximate edge 105 of hydrophilic article 100. In such an embodiment, fluid can be introduced into fluid transport channel 140 by simply contacting the fluid with landing zone 150, e.g., by contacting edge 105 with the fluid. The open area in spacer layer 130 at edge 105 permits fluid to contact landing zone 150 and enter fluid transport channel 140.

In some embodiments, the landing zone is located at a position away from the edge of the article. Regardless of its location, in some embodiments, the landing zone may be covered or otherwise protected from fluid contact until use. In such embodiments, it may be necessary to breach such a cover, e.g., by piercing or removing at least a portion of the cover to expose the landing zone to fluid.

Generally, fluid transport channel 140 defines a path for fluid to travel by capillary action along hydrophilic layer 120 from a landing zone to another desired location, e.g., detection zones 170 and 175. As used herein, "detection zone" refers to a location in the fluid path where one or more properties of the fluid can be detected. For example, in some embodiments, a detection zone may be a location where the fluid can be optically interrogated. For example, light (UV, IR, visible, and the like) may be directed at the fluid and the fluids interaction with the light (e.g., absorption, scatter, reflection, and the like) may be detected and optionally recorded.

In some embodiments, an electrochemical sensor may be used for detection. An electrochemical sensor is a device configured to detect the presence of, and/or measure the concentration of, an analyte by way of electrochemical oxidation and reduction reactions within the sensor. In some embodiments, the hydrophilic article includes an electrode system comprising a set of measuring electrodes, e.g., at least a working electrode and a counter electrode, within the detection zone. The detection zone may be configured such that sample fluid entering the chamber is placed in electrolytic contact with both the working electrode and the counter electrode. This allows electrical current to flow between the measuring electrodes to affect the electrooxidation or electroreduction of the analyte.

In some embodiments, the hydrophilic article includes a chemical reagent for reacting with the test analyte to produce the electrochemical signal that represents the presence of the analyte in the sample fluid. For example, the reagent may be located in one or more of the landing zone, the detection zone, or at a location along the fluid transport channel. In some embodiments, the reagent may be coated on, or present within one or more surfaces defining the landing zone, the detection zone, or the fluid transport channel. In some embodiments, the reagent can include a variety of active components selected to determine the presence and/or concentration of various analytes. The test chemistry is therefore selected in respect to the analyte to be assessed. The selection of an appropriate chemistry, such as one or more enzymes, co-enzymes, and co-factors is well within the skill in the art.

In some embodiments, hydrophilic films of the present disclosure can also be used in the manufacture of microfluidic devices to assist with fluid movement within and along the device via capillary flow action. An exemplary microfluidic device is described in U.S. Pat. No. 6,375,871 ("Methods of Manufacturing Microfluidic Articles"). Such devices may comprise capillary channels within a base or spacer layer which is covered with a hydrophilic film. Such devices can be used for purification or analysis of chemical or biological components. Examples of such methods performed in microfluidic devices include but are not limited to sample preparation, cell sorting, capture, and detection, colorimetric or fluorescent detection assays, nucleic acid analysis, immunoassays, blood chemistry analysis, temperature controlled biological reactions such as polymerase chain reaction (PCR). These devices and assays or detection methods are well-known to those skilled in the art.

Another feature that may be present in the fluid transport channels of some embodiments of the present disclosure are illustrated by wells 160 and 165. Such wells may contain a component that reacts with or otherwise alters a property of the fluid being transported, e.g., one or more of chemical reagents. Such a component may be held within the well and/or coated or otherwise applied to an exposed surface of the well. In some embodiments, the component may not be present in the well until use, e.g., the component can be injected into the well.

In some embodiments, the well may be located upstream of the detection zone. For example, well 165 is located upstream of detection zone 175. Fluid entering fluid transport channel 140 at landing zone 150 will be transported along hydrophilic layer 120 to well 165. Here the fluid will contact any component present within the well. The fluid will then continue traveling by capillary action into detection zone 175, where features of the fluid, including features potentially modified by the component, may be detected.

Alternatively, the combination of the component on well 160 with the fluid may occur in detection zone 170. Here, fluid is transported from landing zone 150 to detection zone 170. A component is independently transported, e.g., moved from well 160 into detection zone 170, where it reacts or otherwise interacts with the fluid. Again, features of the fluid, including features potentially modified by the component, may be detected.

As illustrated in FIGS. 2 and 3, detection zones 170 and 175 and/or wells 160 and 165 may include a variation in the general cross-section of fluid transport channel 140. For example, detection zone 170 and 175 are illustrated as cubes, while wells 160 and 165 are illustrated as cylinders. However, the detection zones and or wells can be of any desired shape, and may or may not include any variation in the cross-section of the fluid transport channel.

Figure 5:
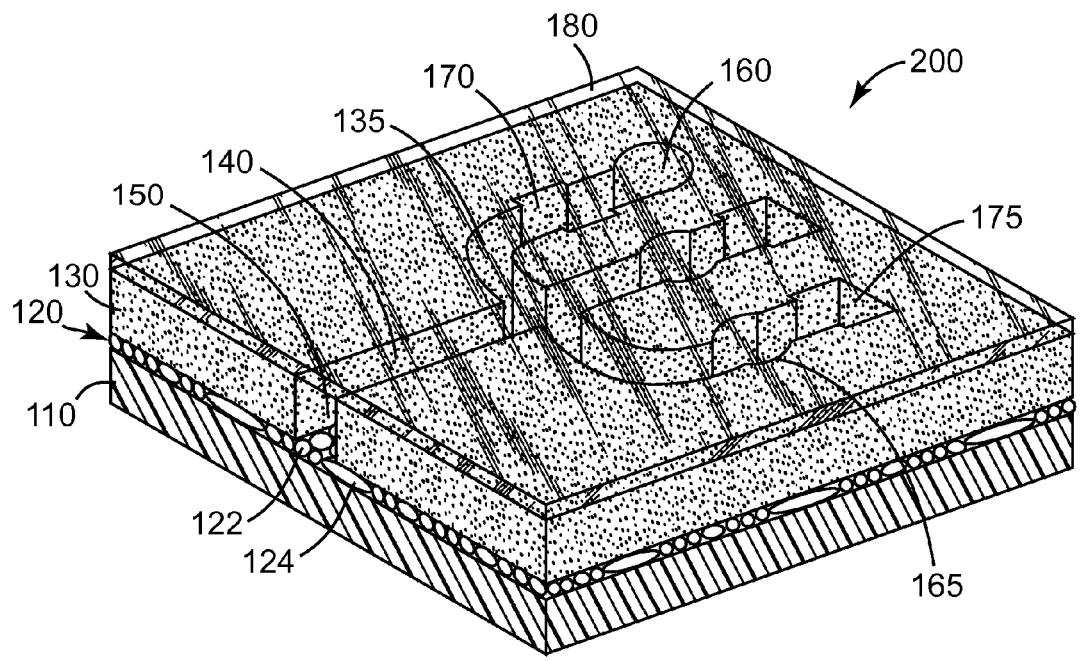
FIG. 5 illustrates a perspective view of the exemplary hydrophilic article of FIG. 4 according to some embodiments of the present disclosure.

FIGS. 4 and 5, illustrate cover layer 180, another optional feature that may be beneficial in some embodiments of the present disclosure. In some embodiments, it may be desirable to minimize or prevent access to the fluid transport channel. For example, to avoid contamination, access to the channel may be restricted to certain specific location such as the landing zone. Cover layer 180 illustrates one potential means to prevent undesired contact with the fluid transport layer. In some embodiments, cover layer 180 is in contact with the surface of spacer layer 130, opposite hydrophilic layer 120. In some embodiments, cover layer 180 covers all or substantially all of spacer layer 130. In some embodiments, the cover layer may only cover portions of the spacer layer, e.g. the cover layer may cover all or select portions of fluid transport channel 140, contacting the spacer layer to the extent necessary or desired to maintain its position.

Depending on the intended use, the cover layer may be positioned so as to leave portions of the fluid transport channel exposed, e.g., at one or more of a landing zone, a well or a detection zone. In some embodiments, all or a portion of the cover layer may be releasably attached to the spacer layer. For example, in some embodiments, the entire cover layer may be removed when desired, e.g., just prior to use. In some embodiments, select portions of the cover layer may be removed when desired. For example, a portion of the cover layer may be removed to expose one or more of a landing zone, a well, or a detection zone.

Generally, any suitable material may be used for the cover layer including, e.g., paper, polymeric films, woven and non-woven webs, metal foils, multilayer constructions and the like, including combinations thereof. In some embodiments, the cover layer may be a hydrophilic film. For example, in some embodiments, the cover layer may be the same or similar to hydrophilic layer 120. For example, cover layer 180 may include a substrate with hydrophilic layer 120 adhered, directly or indirectly to a substrate and positioned relative to the spacer layer such that the hydrophilic layer forms a boundary of the fluid transport channel. Generally, if the cover film is to remain intact covering the detection zone, the cover layer should not substantially interfere with detection means. For example, when optical detection means are used, the cover layer should permit sufficient transmission of the appropriate frequency of light to permit detection.

Figure 6:
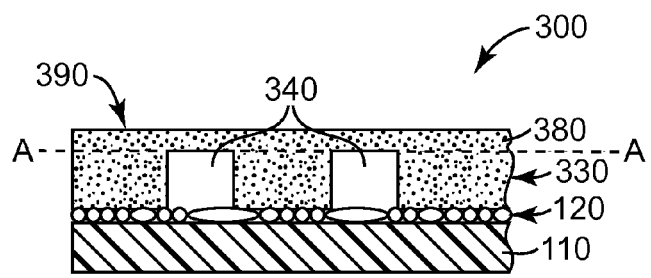
FIG. 6 illustrates an edge view of yet another exemplary hydrophilic article according to some embodiments of the present disclosure.

FIG. 6 illustrates an edge view of yet another exemplary embodiment of the hydrophilic articles of the present disclosure. Hydrophilic article 300 comprises first substrate 110, hydrophilic layer 120, and second substrate 390 comprising spacer layer 330 and cover layer 380. In this embodiment, spacer layer 330 is integral to cover layer 380. In some embodiments, substrate 390 may be modified, e.g., embossed, etched, ground, molded, etc., to form fluid transport channels 340 in substrate 390. Generally, the modified region below dashed line A-A is referred to as the spacer layer, while the unmodified region is referred to as the cover layer. As in previous embodiments, Hydrophilic layer 120 is adhered to spacer layer 330 such that fluid transport channels 340 are bounded on one side by the hydrophilic layer. Generally, second substrate 390 may be bonded, directly or indirectly, to hydrophilic layer 120.

The hydrophilic layer comprises acidified, sintered silica nanoparticles such as those described in U.S. Publication 2010/0035039 (U.S. application Ser. No. 12/187,977, filed Aug. 7, 2008, "Acicular Silica Coating for Enhanced Hydrophilicity/Transmissivity").

As used herein, "nanoparticles" means particles having a major dimension of no greater than 200 nm, e.g., no greater than 150 nm, no greater than 100 nm, or even no greater than 50 nm. In some embodiments, the nanoparticles comprise substantially spherical nanoparticles, i.e., nanoparticles having a ratio of major dimension to minor dimension of no greater than 2, in some embodiments, no greater than 1.5, or even no greater than 1.2. In some embodiments, the substantially spherical nanoparticles have an average diameter of no greater than 50 nm, no greater than 40 nm, no greater than 20 nm, no greater than 10 nm, or even no greater than 5 nm.

In some embodiments, a multimodal distribution of spherical nanoparticles may be used. Generally, such multimodal distributions include at least one peak having an average diameter of no greater than 40 nm. Such multimodal distributions include at least peak, and in some embodiments multiple additional peaks having an average diameter of greater than 40 nm, e.g., greater than 100 nm, greater than 200 nm, or even greater than 300 nm. Generally, such multimodal distributions include at least 1 wt. % of nanoparticles in the at least one peak having an average diameter of no greater than 40 nm, e.g., at least 5 wt. % or even at least 10 wt. %.

In some embodiments, the nanoparticles comprise elongated nanoparticles. In some embodiments, the elongated nanoparticles have a ratio of length to average cross-sectional diameter of at least 2, in some embodiments, at least 3, at least 5, or even at least 10. In some embodiments, the ratio of length to average cross-sectional diameter is no greater than 20, e.g., no greater than 15. In some embodiments, the ratio of length to average cross-sectional diameter ranges from 2.5 to 20, inclusive, e.g., 3 to 15, inclusive.

In some embodiments, the hydrophilic layer comprises only substantially spherical nanoparticles. In some embodiments, only elongated nanoparticles may be used. However, as illustrated in FIGS. 1 to 3, in some embodiments, hydrophilic layer 120 incorporates both substantially spherical nanoparticles 122 and elongated nanoparticles 124. In some embodiments, the hydrophilic layer contains at least 30 wt. %, e.g., at least 40 wt. %, at least 50 wt. % or even at least 60 wt. % substantially spherical nanoparticles, based on the total weight of nanoparticles. In some embodiments, the hydrophilic layer comprises at least 2 wt. %, e.g., at least 5 wt. %, at least 10 wt. %, at least 30 wt. %, or even at least 50 wt. % elongated nanoparticles, based on the total weight of nanoparticles. In some embodiments, the hydrophilic layer comprises 40 to 98 wt. %, e.g., 50 to 95 wt. %, inclusive spherical nanoparticles and, correspondingly, 2 to 60 wt. %, e.g., 5 to 50 wt. % elongated nanoparticles.

Generally, the silica nanoparticles are substantially free of organic surface modifying agents, i.e., organic compounds ionically or covalently bonded to the surface of the silica nanoparticles. As a practical matter, it can be difficult or even impossible to avoid the presence of trace amounts of organic material ionically or covalently bonded to the surface of the silica nanoparticles. However, the unmodified silica nanoparticles of the present disclosure are substantially free of such materials, i.e., if present at all, the surface modifier loading is no greater than 5% of the theoretical loading required for 100% surface coverage, e.g., less than 2%, or even less than 1% of such theoretical loading. In some embodiments, the silica nanoparticles are free of any organic surface modifying agents.

Generally, the hydrophilic layer can be prepared by acidifying the silica nanoparticles in a coating solution, applying the coating solution to the surface of a substrate, and drying the coating to provide a hydrophilic layer comprising acidified, sintered silica nanoparticles. Inorganic silica nanoparticles in aqueous media (sols) are well known in the art and available commercially. Silica sols in water or aqueous alcohol solutions are available commercially under such trade names as LUDOX (manufactured by E.I. du Pont de Nemours and Co., Inc., Wilmington, Del., USA), NYACOL (available from Nyacol Co., Ashland, Mass.), SNOWTEX (manufactured by Nissan Chemical America Corporation, Houston, Tex.), and NALCO (manufactured by Nalco Chemical Co., Naperville, Ill. USA). Non-aqueous silica sols (also called silica organosols) may also be used and are silica sol dispersions wherein the liquid phase is an organic solvent. Such organosols are available from Nissan Chemical.

The coating composition may be acidified to the desired pH level with an acid having a pKa ($H_2O$) of less than 5, in some embodiments, less than 2.5, e.g., less than 1. Useful acids include both organic and inorganic acids and may be exemplified by oxalic acid, formic acid, $H_2SO_3$, $H_3PO_4$, $CF_3CO_2H$, HCl, HBr, HI, $HBrO_3$, $HNO_3$, $HClO_4$, $H_2SO_4$, $CH_3SO_3H$, $CF_3SO_3H$, $CF_3CO_2H$, and $CH_3OSO_2OH$. In some embodiments, preferred acids include HCl, $HNO_3$, $H_2SO_4$, and $H_3PO_4$. In some embodiments, it is desirable to provide a mixture of an organic and inorganic acid. In some embodiments one may use a mixture of acids comprising those having a pKa of no greater than 5 (in some embodiments, no greater than 2.5, or even no greater than 1) and minor amounts of other acids having a pKa greater than 5. In some embodiments, the coating composition generally contains sufficient acid to provide a pH of less than 5, in some embodiments, less than 4, or even less than 3.

Light-scattering measurements on these acidified dispersions indicate that these silica particles tend to agglomerate, providing (after coating and drying) three-dimensional porous networks of silica particles where each particle appears to be firmly bonded to adjacent particles. Surprisingly, the acidified dispersions appear to be stable when the pH is in the range 1 to 3. Light-scattering measurements showed that these agglomerated, acidified silica particles at pH ~2 to 3 and at 10 wt. % concentration retained the same size after more than a week or even more than a month, although deformation in the shape is noted. Such acidified silica particle dispersions would be expected to remain stable even much longer at lower dispersion concentrations.

In some embodiments, a porous network of silica nanoparticles is obtained by acid sintering of the agglomerated silica nanoparticles as the water or solvent evaporates and the acid concentration increases. Electron micrographs reveal such bonds as silica "necks" between adjacent particles which are created by the acid in the absence of silica sources such as tetraalkoxysilanes or siloxane oligomers. Their formation is attributed to the catalytic action of strong acid in making and breaking siloxane bonds.

In some embodiments, alternatively or additionally, the silica nanoparticles can be sintered with a heat treatment (e.g., flame treatment). Heat treatment can be conducted, for example, by passing the structured substrate under a flame (burner) for typically about 1-3 seconds, or even longer provided the substrate is not subjected to conditions that melt the substrate. Other techniques of heating may also include, for example, infra-red heaters, and hot air blowers. The surface opposite the coated surface can be cooled, for example, by a chilled metal roll or via liquid application to enable longer residence times under the flame.

In some embodiments, the coatings of the present invention are applied to achieve a uniform average dry thickness between 50 and 1000 nm, inclusive, preferably 75 to 400 nm, and more preferably 100 to 300 nm, inclusive, as measured using an ellipsometer such as a Gaertner Scientific Corp Model No. L115C.

The compositions may be coated on the article using conventional techniques, such as bar, roll, curtain, rotogravure, spray, or dip coating techniques. In order to ensure uniform coating and wetting of the film, it may be desirable to oxidize the substrate surface prior to coating using corona discharge or flame treatment methods. Other methods capable of increasing the surface energy of the article include the use of primers.

The articles of the disclosure include a substrate bearing a continuous network of silica particle agglomerates. As used herein, the term "continuous" refers to covering the surface of the substrate with virtually no discontinuities or gaps in the areas where the gelled network is applied. Thus, e.g., if the silica particles are pattern-coated, uncoated regions may be created, yet the coating would be considered "continuous" provided there were virtually no discontinuities or gaps in the areas where the gelled network is applied. The term "network" refers to an aggregation or agglomeration of acicular silica particles linked together to form a porous three-dimensional network.

The nanoporosity of the sintered nanosilica coating leads to high hydrophilicity, e.g., superhydrophilicity. According to ASTM D7334-08, an advancing contact angle of less than 45 degrees in indicative of wetting, while advancing contact angles of less than 20 degrees are indicative of excellent wetting. A typical silica glass surface exhibits a water contact angle of 37-43 degrees. However the highly porous acid-sintered-nanosilica-coatings exhibit lower water contact angles, e.g., less than 10 degrees, in less than 0.5-2 seconds, in part because of the nanowicking of water into the network of capillaries present in the coatings. Generally, the apparent water contact angle of a liquid on a surface is dependent upon the roughness of the surface. In particular, as roughness increases, the apparent contact angle decreases. For a nanoporous surface, the roughness approaches infinity, and any liquid having a contact angle of less than 90 degrees on a smooth surface, will have a contact angle approaching zero on a nanoporous surface resulting in complete wetting of the nanoporous surface.

In some embodiments, a resin, e.g., a polymeric resin, may be present in the hydrophilic layer. However, in many applications the use of resin may be undesirable, e.g., components of the resin may leach into the fluid as it contacts the hydrophilic layer. In some embodiments, the hydrophilic layer comprises no greater than 5 weight percent (5 wt. %) resin, e.g., no greater than 2 wt. %, or even substantially no resin, based on the total weight of the hydrophilic layer. As used herein, substantially no resin means that the hydrophilic layer is free of resin except for any trace amounts that may be present due to, e.g., normal material supply and manufacturing processes.

In some embodiments, the hydrophilic layer comprises at least 95 weight percent of the nanoparticles, e.g., at least 98 wt. % nanoparticles based on the total weight of the hydrophilic layer. In some embodiments, the hydrophilic layer consists essentially of the nanoparticles. For example, in some embodiments, the hydrophilic layer comprises at least 95 weight percent of the nanoparticles and no greater than 5 wt. % resin, e.g., at least 98 wt. % nanoparticles and no greater than 2 wt. % resin, based on the total weight of the hydrophilic layer.

In general, the hydrophilic articles of the present disclosure may be used to transport fluids, including, e.g., biological fluids. Exemplary biological fluids include blood, urine, sweat, and saliva.

EXAMPLES

Materials. The following Examples used two different silica nanoparticles. "SILICA-SPH" was a substantially spherical colloidal silica having a average diameter of 4 nm (NALCO 1115, available from Nalco, Naperville, Ill.). "SILICA-ELG" was an elongated colloidal silica having a diameter of 9-15 nm and a length of 40-100 nm (SNOWTEX OUP, available from Nissan Chemical, Houston, Tex.).

Contact Angle Procedure. Contact angle was determined per ASTM-D7334-08. Contact angle measurements were made on the coated samples using deionized water using a goniometer (FIBRO System AB, Stockholm, Sweden).

Spreading Drop Procedure. A sample film was conditioned at 23° C./50% RH (relative humidity) for eight hours before and during testing. The film sample was placed on a clean flat horizontal surface with the side to be tested facing up. A 3 microliter drop of deionized water containing 0.07% by weight Wool Fast Brilliant Red R. L. Dye, (Pylam Products, Garden City, N.Y.) was gently placed on the surface with a micropipette. The drop was allowed to spread to its maximum extent and completely dry. The diameter of the dyed area was determined by placing the film over a paper with premeasured circles of varying diameters. The average drop diameter was recorded.

Example 1

A silica coating solution was prepared by combining 70 weight percent of SILICA-SPH with 30 weight percent of SILICA-ELG. A suspension was prepared by mixing 2 to 3 weight % of the resulting combined silica composition with 97 to 98 weight percent water. Nitric acid (commercial grade, obtained from EMD, Gibbstown, N.J.) was added to adjust the pH of the silica coating to 2.5.

The silica coating was applied to a PET film (0.09 mm thick polyethylene terephthalate film, 3M Company, St. Paul, Minn.) using a slot-fed die. The coating was dried at about 130° C., yielding a dried coat weight of 0.3 to 0.4 grams per square meter. The coated film of Example 1 (EX-1) and was subjected to the Contact Angle Procedure and the Spreading Drop Procedure. The results are summarized in Table 1, and compared to results obtained using the same PET, but uncoated (CE-1).

TABLE 1

Contact angle and spreading drop results for examples EX-1 and CE-1.

| Example | Contact Angle (degrees) | Drop Diameter (mm) |
|---------|-------------------------|--------------------|
| EX-1    | 8                       | 8.1                |
| CE-1    | 54                      | 4.9                |

The sample of Example 1 was subjected to several conditions to assess the durability of the coatings. The results were compared to a commercially available hydrophilic film comprises a PET substrate with a conventional organic hydrophilic coating (3M™ Hydrophilic Polyester Film 9962, "CE-2"). Film samples were immersed into either a 25° C. or a 90° C. water bath for five minutes. Once dried, the contact angle was measured. Mean result for replicate measurements on the films of EX-1 and CE-2 are shown in Table 2.

TABLE 2

Contact angle (degrees) for EX-1 and CE-1.

| Test | EX-1 Contact Angle | | CE-2 Contact Angle | |
|------|--------|-------|--------|-------|
|      | Before | After | Before | After |
| Water Immersion | | | | |
| 25° C. | 8.2 | 11 | 14.2 | 43 |
| 90° C. | 8.2 | 13 | 14.2 | 59 |

The present inventors have surprisingly discovered that the hydrophilic layer retains its hydrophilic properties after immersion in water. One advantage of a device comprising a hydrophilic surface which retains its hydrophilic properties after exposure to liquids is that the surface chemistry does not solubalize and contaminate the test fluid. Another advantage of a fluid transport device comprising a reusable hydrophilic layer is that fluid can pass over the film multiple times and fluid flow will not be compromised, such as in lab-on-a-chip assays involving but not limited to washing or fluid separation steps. Surprisingly the hydrophilic coating in this invention retained its hydrophilic properties after immersion in 90 degree Celsius water, which is advantageous for use in devices which require elevated temperatures for analyte testing such as polymerase chain reaction.

EX-1 was also evaluated for resistance to wiping (abrasion) by applying 3 or 10 wipes with a tissue (KIMTECH wipes, available from Kimberly-Clark Corporation, Irving, Tex.). After wiping, contact angle and spreading drop were measured. Finally, accelerated stability of EX-1 was assessed by placing the example films in chambers held at 24° C./60% Relative Humidity ("60% RH") and 49° C./dry for 8 weeks. Afterward, contact angle and spreading drop were measured. Mean result for replicate measurements are shown in Table 3.

TABLE 3

Contact angle and spreading drop results for EX-1.

| Test | Contact Angle (degrees) | | Spreading Drop (mm) | |
| --- | --- | --- | --- | --- |
| | Before | After | Before | After |
| Abrasion | | | | |
| 3 wipes | 7.8 | 15 | 8.1 | 6.9 |
| 10 wipes | 7.8 | 19 | 8.1 | 5.9 |
| 8 Week Stability | | | | |
| 24° C./60% RH | 8.2 | 14 | 8.1 | 8.5 |
| 49° C./dry | 8.2 | 18 | 8.1 | 8.0 |

What is claimed is:

1. A hydrophilic article comprising a substrate, a first surface of a hydrophilic layer comprising sintered, acidified silica nanoparticles attached to the substrate, and a spacer layer attached to a first portion of a second surface of the hydrophilic layer opposite the first surface, wherein the spacer layer defines at least one fluid transport channel bounded on one side by a second portion of the second surface of the hydrophilic layer, wherein the nanoparticles comprise elongated silica nanoparticles having an average length to diameter ratio of at least 2, and wherein the hydrophilic layer is substantially surfactant-free.

2. The hydrophilic article of claim 1, wherein the hydrophilic layer comprises no greater than 0.001 weight percent surfactant, based on the total weight of the hydrophilic layer.

3. The hydrophilic article of claim 2, wherein the hydrophilic layer comprises no greater than 0.0005 weight percent surfactant, based on the total weight of the hydrophilic layer.

4. The hydrophilic article according to claim 1, wherein the fluid transport channel comprises a landing zone comprising an exposed portion of the hydrophilic layer.

5. The hydrophilic article of claim 4, wherein the landing zone is located at an edge of the substrate.

6. The hydrophilic article of claim 1, wherein the fluid transport channel comprises a detection zone comprising a portion of the hydrophilic layer that is (i) exposed or (ii) covered by a layer having a transmissivity of at least 50% for at least one wavelength of electromagnetic energy between 200 and 800 nm, inclusive.

7. The hydrophilic article according to claim 6, wherein the article comprises the landing zone, and wherein the detection zone is in fluid communication with the landing zone via the transport channel.

8. The hydrophilic article according to claim 1, further comprising a cover layer in contact with at least a portion of a surface of the spacer layer opposite the hydrophilic layer and covering at least a portion of the fluid transport channel.

9. The hydrophilic article of claim 8, wherein the cover layer comprises a second hydrophilic layer comprising sintered, acidified silica nanoparticles attached to a second substrate.

10. The hydrophilic article of claim 8, wherein the cover layer is integral with the spacer layer.

11. The hydrophilic article of claim 1, wherein the average length to diameter ratio of the elongated silica nanoparticles is 3 to 15.

12. The hydrophilic article according to claim 1, wherein the nanoparticles comprise 50 to 95 weight percent substantially spherical silica nanoparticles having a ratio of maximum diameter to minimum diameter of less than 2, and 5 to 50 parts by weight elongated silica nanoparticles having an average length to diameter ratio of at least 2, based on the total weight of the nanoparticles.

13. The hydrophilic article of claim 12, wherein the ratio of maximum diameter to minimum diameter of the substantially spherical silica nanoparticles is less than 1.2 and the average length to diameter ratio of the elongated silica nanoparticles is 3 to 15.

14. The hydrophilic article of claim 13, wherein the nanoparticles comprise 60 to 80 weight percent of the substantially spherical nanoparticles and 20 to 40 parts by weight of the elongated nanoparticles, based on the total weight of the nanoparticles.

15. The hydrophilic article according to claim 1, wherein the hydrophilic layer comprises at least 95 weight percent of the nanoparticles, based on the total weight of the hydrophilic layer.

16. The hydrophilic article of claim 15, wherein the hydrophilic layer comprises no greater than 2 weight percent resin, based on the total weight of the hydrophilic layer.

17. The hydrophilic article according to claim 16, wherein the hydrophilic layer consists essentially of the nanoparticles.

18. A method of transporting a fluid with the hydrophilic article according to claim 1 comprising: applying the fluid to a first region of the second portion of the second surface of the hydrophilic layer and wicking the fluid within the fluid transport channel from the first region to a second region of the second portion of the second surface of the hydrophilic layer.

19. The method of claim 18, wherein the fluid is a biological fluid.

* * * * *